United States Patent [19]
Katschnig et al.

[11] Patent Number: 5,407,641
[45] Date of Patent: Apr. 18, 1995

[54] MICROWAVE APPARATUS, AND CONTAINER FOR USE IN A MICROWAVE APPARATUS

[75] Inventors: Helmut Katschnig, Burgstrasse 108, 8750 Judenburg; Leonard Gagea, Vienna, both of Austria

[73] Assignee: Helmut Katschnig, Austria

[21] Appl. No.: 122,708

[22] Filed: Sep. 16, 1993

Related U.S. Application Data

[63] Continuation-in-part of Ser. No. 782,249, Oct. 23, 1991, Pat. No. 5,246,674.

[30] Foreign Application Priority Data

| Oct. 25, 1990 | [AT] | Austria | 2164/90 |
| Dec. 7, 1990 | [AT] | Austria | 2487/90 |
| Apr. 29, 1991 | [AT] | Austria | 894/91 |
| Jun. 26, 1991 | [AT] | Austria | 1282/91 |

[51] Int. Cl.$^6$ ............................ G05D 23/00
[52] U.S. Cl. ................. 422/107; 219/679; 219/686; 219/710; 422/295; 422/302; 422/307
[58] Field of Search ............... 422/307, 294, 295, 302, 422/21, 107; 219/678, 679, 710, 734, 735, 686

[56] References Cited

U.S. PATENT DOCUMENTS

| 3,839,616 | 10/1974 | Risman | 219/707 |
| 4,406,861 | 9/1983 | Beauvais et al. | 422/302 |
| 4,490,597 | 12/1984 | Mengel | 219/735 |
| 4,613,738 | 9/1986 | Saville | 219/686 |
| 4,796,776 | 1/1989 | Dalquist et al. | 219/686 |
| 4,857,686 | 8/1989 | Hirata et al. | 219/710 |
| 4,871,891 | 10/1989 | Steers et al. | 219/710 |
| 4,877,624 | 10/1989 | Floyd et al. | 219/686 |
| 4,952,765 | 8/1990 | Toyosawa | 219/735 |
| 4,998,000 | 3/1991 | Halloran | 219/734 |
| 5,108,701 | 4/1992 | Zakaria et al. | 422/21 |

FOREIGN PATENT DOCUMENTS 0198430 10/1986 European Pat. Off. .

*Primary Examiner*—W. Gary Jones
*Assistant Examiner*—Laura E. Edwards
*Attorney, Agent, or Firm*—Henry M. Feiereisen

[57] ABSTRACT

A container for use in a microwave apparatus, in particular for heating, drying, disinfecting and/or sterilizing of materials, objects, liquids or the like, includes a lid securely attachable via a pressure lock to the container and including connections for allowing attachment of various valves, pumps etc. to monitor and influence conditions in the container. The connections are self-sealing plug connector pipes which are engageable with a complementary coupler piece of the microwave apparatus. The microwave apparatus includes an injector unit by which water or other liquid is introduced into the material to be treated, with the amount of injected water being dependent on the water content of the material. The injector unit includes a nozzle head which projects into the treatment chamber of the microwave apparatus and incorporates sensors for determining physical and/or chemical parameters.

3 Claims, 8 Drawing Sheets

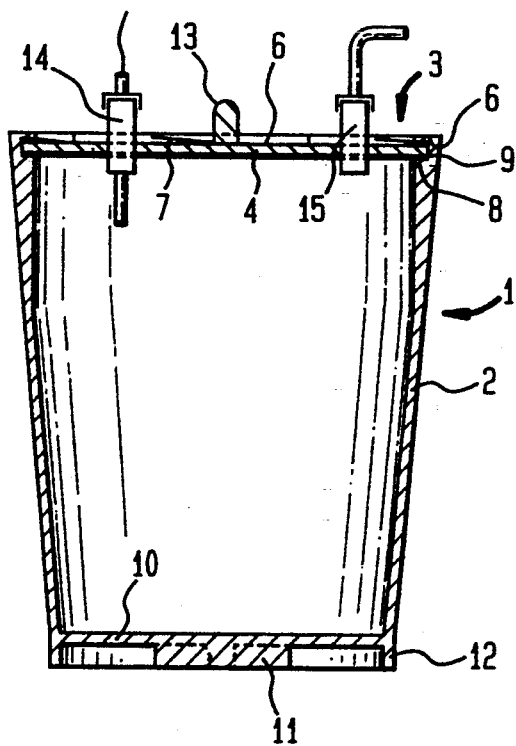
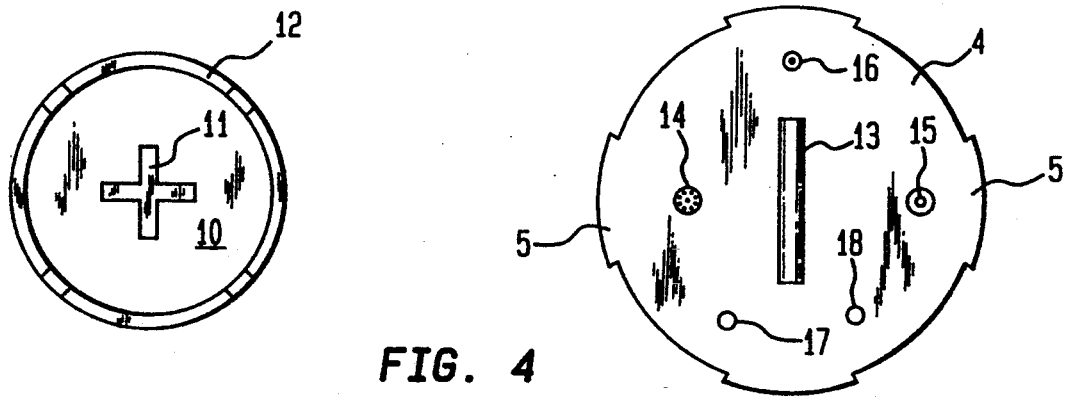
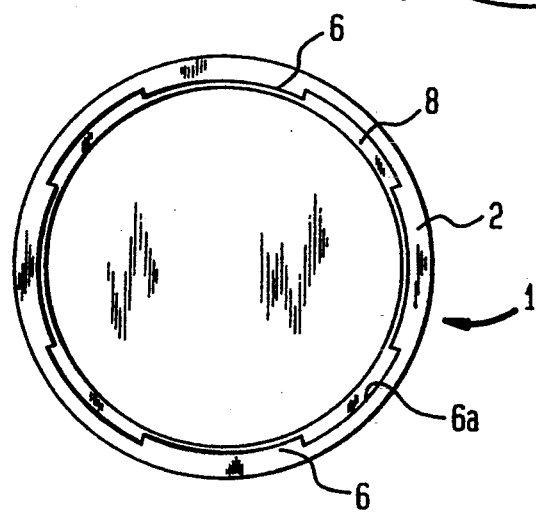

MICROWAVE APPARATUS, AND CONTAINER FOR USE IN A MICROWAVE APPARATUS

This is a continuation-in-part of application Ser. No. 07/782,249, filed Oct. 23, 1991, now U.S. Pat. No. 5,246,674.

BACKGROUND OF THE INVENTION

The present invention refers to a microwave apparatus, and to a container for use in a microwave apparatus, in particular for heating, drying, disinfecting and/or sterilizing materials, objects, liquids or the like.

Microwave apparatuses are used for heating, disinfecting or sterilizing various materials such as i.a. refuse from hospitals, kitchen garbage etc. In order to prevent a burning of the material during microwaving, it is known to add liquid such as water, possibly together with disinfectants and/or odorants, to the material, e.g. by placing a separate liquid source, e.g. a bag of water with or without disinfectant and/or odorant, within the interior of the treatment chamber. This proposal allows only a fixed amount of water to be placed in the chamber before starting the microwaving and does not consider the type of material to be treated. This is disadvantageous because if the amount of water is too large, great energies for heating, disinfecting or sterilizing the material are wasted. Moreover, a large amount of liquid is retained, thus requiring a targeted disposal of increased amounts of liquids. Apart from that, the provision of large amounts of liquid prolong the treatment cycle, thus rendering the overall performance of the unit uneconomic. On the other hand, when the amount of liquid placed in the treatment chamber is too low, dry refuse or other material to be treated may ignite, resulting in a possible destruction of the unit.

In general, the material is placed in containers which are sufficiently transparent to microwaves to allow energy to pass through and to treat the material. With these containers, a particular treatment such as overpressure or underpressure treatment is, however, not possible.

European publication EP-A1 88 700 describes an apparatus in which a jar containing a food product is placed on a base and enclosed by a bell-shaped cover which is connectable to the base via a bayonet mount. This unit is placed in a microwave oven for heating. For limiting the maximum pressure within the enclosure during heating and for preventing entry of air during subsequent cooling, a pressure control check valve is provided at the top of the cover. GB-PS 1,269,606 describes a container with end walls which are detachably secured to the container via a bayonet mount and provided with respective openings which are closed by pressure relief valves. These containers, even though representing an improvement over conventional cookware generally employed in connection with microwave ovens, are still limited to their use and do not allow particular treatment of the material, monitoring of the material and monitoring of prevailing conditions within the container.

SUMMARY OF THE INVENTION

It is thus an object of the present invention to provide an improved microwave apparatus obviating the afore-stated drawbacks.

It is further an object of the present invention to provide an improved container for use in a microwave apparatus, obviating the afore-stated drawbacks.

These objects and others which will become apparent hereinafter are attained in accordance with the present invention by providing the microwave apparatus with an liquid injector unit for directly adding liquid to the material in dependence of the water content of the material to be treated. In this manner, the required amount of liquid depending on the actual liquid content of the material can be added so that for all circumstances a sufficient amount of liquid is obtained for treating the material.

Advantageously, the water content of the material can be determined by a measuring instrument which is responsive to the weight of the material. The determination is based on the assumption that the weight of the material is essentially defined by its liquid content. This assumption holds generally true for hospital refuse or the like to be disinfected or sterilized whereby the measuring instrument can be supplied with data reflective of the type of material to be treated.

The measuring instrument may be a weighing cell which is connected with the control system for the liquid injector unit so as to attain an automatic and direct addition of liquid in dependence of the weight of the material. It is however also possible to consider the material to be treated by running the control system for the liquid injector in accordance with an algorithm by which the actual liquid content is considered. Thus, the addition of liquid can be adjusted in an optimum manner to the material to be treated whereby the control system can use different algorithms for differently treated materials.

In order to avoid an adverse effect of microwave radiation, it is preferred to arrange the weighing cell outside the resonance space of the microwaves, with a scale plate suitably connected to the weighing cell and arranged in the treatment chamber for supporting the container.

According to a further feature of the present invention, the liquid injector may be arranged within the treatment chamber so that addition of water can occur without requirement of any external manipulation as soon as the container is placed in the treatment chamber and the weight of the material has been determined.

Preferably, the liquid injector is made of microwave-impervious material, and is situated in an opening of the treatment chamber, with the nozzle head of the injector projecting in the interior of the treatment chamber and incorporating sensors for determining physical and/or chemical parameters. In this manner, sensors which are sensitive to high frequency fields are arranged within a shielded area while still being in direct connection with the interior of the treatment chamber as the injector sits in the opening of the treatment chamber, with its nozzle head, which is provided with the sensors, projecting into the interior thereof.

Advantageously, the nozzle head may be provided as temperature sensor i.e. the wall surface of the head acts in certain areas as temperature transmitter for the respective sensor. Certainly, pressure devices for selecting the internal pressure in the chamber may be provided at the wall surface of the nozzle head, or other devices such as pH electrode, oxygen electrodes and the like or devices for detecting chemical conditions within the container. The nozzle head may also be designed as pressure sensor, with the wall surface or parts thereof being preferably provided as pressure membrane so that the material can be pressure-treated in a controlled manner in a suitable container. In the event, the container is not pressure-proof, possible overpressure can be controlled by a suitable pressure relief valve.

In accordance with a further feature of the present invention, a container in accordance with the present invention includes a lid adapted for closing the body of the container, with the lid being tightly secured to the body of the container by means of a pressure lock and provided with fittings and connections for allowing selective attachment of various elements such as elements for applying an overpressure or underpressure, or for monitoring process parameters during treatment. Exemplary elements or devices for attachment include pressure valves, gas inlet valves or gas outlet valves, thermometer etc.

The use of such a container allows a pressure treatment, with the moist material inside the container being heated up until steam development causes an overpressure which is usable for treating the material. In case an underpressure treatment is desired, a vacuum can easily be applied to the container by using one of the connections or fittings.

Suitably, the lid is securely connected to the body of the container via a bayonet mount so as to attain a uniform distribution of the sealing pressure over the circumference of the container.

Preferably, for blending the material within the container, the inside wall surface of the container includes inwardly projecting ribs preferably with rounded ends and/or edges to prevent a destruction of plastic sacks when being used inside the container for holding the material. The ribs may be randomly oriented or designed, e.g. of helical shape, and may extend in a same direction, or in opposite direction, or may be alternatively arranged. An opposing arrangement of the ribs creates a same effect as if the container is turned in different rotational directions. Also, the ribs may be continuous or sectionized to attain in addition to the normal turbulent mixing an upward and downward transport of liquid or pulpy material along the wall surface. Discontinuous rib sections also considerably simplify the emptying of the container.

In order to prevent a slipping off or a rotation of the container relative to the turntable of the microwave apparatus, the bottom of the container includes engaging means which cooperate with complementary elements of the turntable. For example, the bottom of the container may include pins or ribs engaging respective recesses of grooves in the turntable. It is also possible to provide the bottom with peripheral rails by which the perimeter of the turntable is externally grasped to hold the container securely upon the turntable.

Preferably, the container and the lid as well as the connections and fittings are made of microwave-transparent, heat-resistant and pressure-proof material such as teflon, to allow treatment at high temperatures and increased or reduced pressures.

According to another feature of the present invention, the connections and fittings are self-sealing plug connector pipes which are engageable with a complementary coupler piece of the microwave apparatus. In this manner, a tight connection of connecting parts is attained without requiring any additional holding elements.

Preferably, a riser is provided within the interior of the containers and extends from a point slightly above to the bottom of the container to one plug connector pipe for permitting removal of liquid accumulating at the bottom of the container. Also in the event liquid is to be treated, the liquid—after being microwaved and sterilized—can simply be withdrawn and fed to a disposal unit. Suitably, a grid is provided slightly above the lower mouth of the riser at a distance to the bottom for keeping the riser in position and supporting the container and the material. In addition, by providing such a grid, particles escaping or becoming separated from the material to be treated is retained by the grid.

In accordance with a preferred embodiment of the container, the plug connector pipes are mounted in and outwardly project from the body wall to allow tight attachment to the coupler piece of the microwave apparatus when sliding the container toward the coupler piece. Suitably, the bottom of the container is provided with guide means cooperating with complementary elements of the microwave apparatus for correct positioning of the container relative to the microwave apparatus and proper alignment of the plug connectors with the coupler piece. In this manner, the container needs only be pushed into position for attachment of the plug connectors with the coupler piece.

It is, however, also possible to provide the plug connector pipes as a common unit which is secured to the lid of the container, with the complementary coupler piece being flexibly mounted to the microwave apparatus. Such a design allows a closed container to be placed in the microwave apparatus, with the coupler piece being simply attached to the plug connectors. Suitably, the coupler piece includes pressure relief valves or other elements so that separate connections and fittings are not required for the lid.

According to a further modification, the riser, which ends near the bottom at slight distance thereto, may be fixedly secured to the container. In this case, respective sealing surfaces are provided between the upper end of the riser and the lid to obtain a leakage-proof connection between the riser and the pertaining plug connector. When closing the container, the lid is turned until being tightly secured to the container, at which point, the lower mouth of the plug connector, which does not project into the container but is now flush with the inside surface of the lid, is in communication with the upper end of the riser whereby a tight seal is effected therebetween. Thus, in case the plug connector is provided in the lid, there is no need to insert the riser after the material has already been introduced in the container and placed in the microwave apparatus.

According to yet another embodiment of a microwave apparatus in accordance with the present invention, a container is preferably composed of an upper shell and a lower shell which are securely closeable via a seal. The upper shell is provided at its top face with a bore which is sealed off by a clamp block sandwiched between the top face of the upper shell and the opposite top wall of the treatment chamber. The clamp block is pressed downwardly onto the upper shell by an eccentric which runs on the elastic top wall of the treatment chamber. The eccentric is connected to and thus actuatable by a clamping lever via a shaft which is supported in the frame of the microwave apparatus and by a suitable bracket extending across the top wall of the treatment chamber.

The clamp block is suitably provided with a passageway which communicates with the bore in the top face of the upper shell. Waste gas generated during heating of the waste through microwave radiation may exit through the bore in the upper shell and the passageway in the clamp block and pass through a hose and a heat insulated pipe. Placed onto the outside of the pipe is a temperature sensor which is operatively connected to a control unit. The sensor measures the temperature at the wall of the pipe to thereby determine the temperature of the exiting waste gas. If the temperature exceeds a desired value, the energy supply to microwave apparatus is cut.

BRIEF DESCRIPTION OF THE DRAWING

The above and other objects, features and advantages of the present invention will now be described in more detail with reference to the accompanying drawing in which:

FIG. 1 is a schematic vertical section of one embodiment of a container according to the present invention, with smooth inside wall surface;

FIG. 2 is a schematic top view of the container of FIG. 1;

FIG. 3 is a schematic bottom view of the container of FIG. 1;

FIG. 4 is a top view of the container of FIG. 1, with the lid being removed;

DETAILED DESCRIPTION OF PREFERRED EMBODIMENTS

Figure 5:
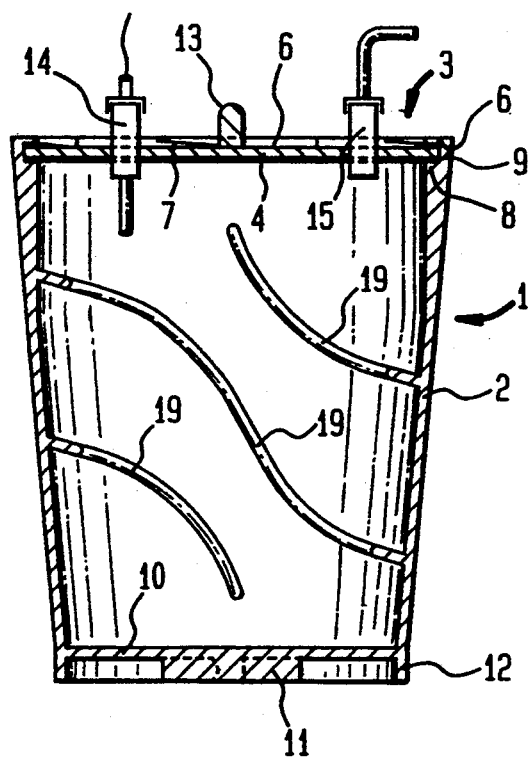
FIG. 5 is a schematic vertical section of the container of FIG. 1, illustrating ribs along the inside wall surface of the container.

Throughout all the Figures, the same or corresponding elements are always indicated by the same reference numerals.

Referring now to the drawing and in particular to FIG. 1, there is shown a schematic vertical section of one embodiment of a container according to the present invention, generally designated by reference numeral 1 and including a body 2 of generally conical configuration. A lid 4 is detachably secured to the container 1 e.g. by means of a bayonet mount generally designated by reference numeral 3. As shown in particular in FIGS. 2 and 4, the lid 4 is provided with plugs 5 which are engageable in recesses 6a spaced about the upper perimeter of the body 2 between projections 6. Extending below the projections 6 of the body 2 are wedge-shaped surfaces 7 (FIG. 1) which end on a circumferential shoulder 8 at the upper end of the body 2. For closing the container 1, the plugs 5 of the lid 4 are aligned with the recesses 6a of the body 2, and the lid 4 is then turned by a handle 13 so that the plugs 5 run along the slanted wedge-shaped surfaces 7 until the lid 4 tightly bears upon the shoulder 8. Suitably, a resilient gasket 9 is interposed between the shoulder 8 and the lid 4 to provide an airtight seal between the lid 4 and the container 1 when the lid 4 is pressed against the gasket 9.

Persons skilled in the art will understand that the type of bayonet mount is shown by way of example only, and may be substituted by any other suitable connection by which the lid can be securely fixed to the container. For example, it is conceivable to provide the lid with a rim which extends over the container perimeter, with the projections of the container being outwardly directed and cooperating with or engaging between inwardly directed plugs of the lid.

In the embodiment of FIG. 1, the inside surface of the body 2 of the container 1 is smooth so as to avoid a destruction of a plastic sack which is placed within the container 1 and filled with material to be treated.

As is further shown in FIGS. 1 and 3, the container 1 has a bottom 10 which is provided at a central location thereof with cross-shaped ribs 11 which engage complementary grooves (not shown) in the turntable of a microwave oven (not shown) so as to attain a secure installation of the container 1 upon the turntable. In addition, the bottom 10 may be provided with circumferential rails 12 by which the turntable of the microwave oven is externally grasped or enveloped to thereby prevent the container 1 from sliding off or being displaced from the turntable. Other means for securing the container upon the turntable are also feasible, e.g. by providing the container with at least one depression for cooperation with a pin of the turntable (not shown).

As is shown in particular in FIG. 2, the lid 4 is further provided with connections and fittings for allowing attachment of various elements, such as a temperature sensor 14, a water connection 15, a relief valve 16 e.g. a pressure relief valve or suction relief valve, a pressure or vacuum connection 17 and a gas connection 18 so as to allow particular treatment of the material inside the container 1 and monitoring of the prevailing conditions.

Turning now to FIG. 5, there is shown a vertical section of a second embodiment of a container according to the present invention, with the container 1 including ribs 19 running along the inside wall surface of the body 2. By means of these ribs 19, liquids or pulpy material contained within the container 1 are blended in a significantly improved manner. The ribs 19 may be randomly oriented or designed e.g. of helical shape and may extend in a same direction, or in opposite direction, or may be alternatively arranged. The opposing arrangement of the ribs results in a same effect as if the container is turned in different rotational directions. Also, the ribs 19 may be continuous or sectionized to attain in addition to the normal turbulent mixing an upward and downward transport of liquid or pulpy material along the wall surface. Discontinuous rib sections also considerably simplify an emptying of the container as the material can easily flow off between the separate ribs. Preferably, the inwardly directed edges and the ends of the ribs 19 are rounded to prevent a destruction of plastic sacks when being used inside of the container 1.

The container 1 is preferably made of a microwave-transparent plastic material which is heat-resistant and pressure-proof. Especially suitable is teflon.

Figure 6:
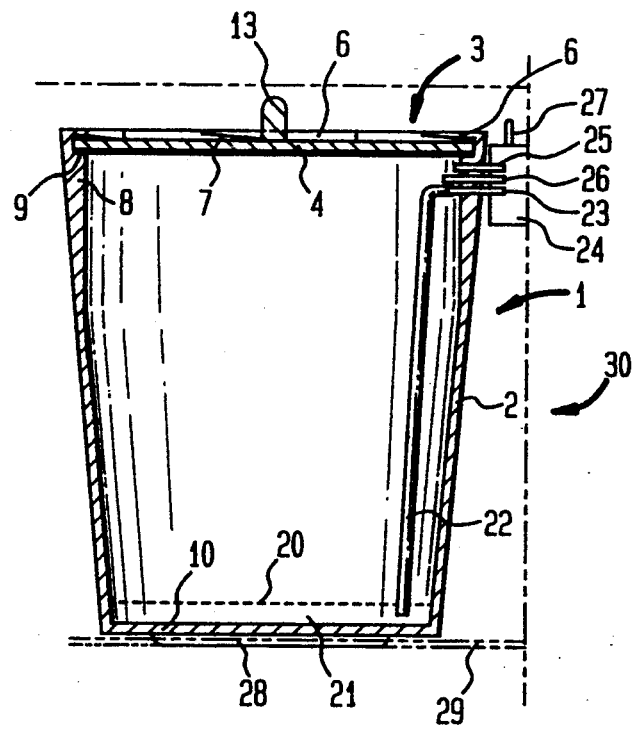
FIG. 6 is a schematic vertical section of another embodiment of a container according to the present invention.

Referring now to FIG. 6, there is shown a vertical section of a variation of the container 1 in which a grid 20 is placed near the bottom 10 for supporting the material or objects within the container 1 and for retaining particles being separated from the material. The grid 20 is arranged inside the container 1 at a slight distance above the bottom 10 to define a space 21 between the grid 20 and the bottom 10. Projecting into the space 21 is the lower end of a riser 22 which runs along the inside wall of the body 2 and is provided for withdrawing and removing liquid which continuously accumulates at the bottom 10 of the container 1. In this manner, liquid removed from the container 1 can be supplied to a disposal unit after being sterilized within the microwave apparatus.

The upper end of the riser 22 is connected to a self-sealing plug connector pipe 23 which is fixedly secured in the body 2 of the container 1 and traverses through respective bores of the body 2 to project outwardly. The plug connector 23 is tightly connectable to a coupler piece 24 which is mounted directly to the microwave apparatus 30 as indicated in FIG. 6 in which the microwave apparatus is shown only in dashdot lines. Extending parallel to the plug connector pipe 23 are further plug connector pipes 25, 26 which can also be brought in tight engagement with the coupler piece 24, with one plug connector pipe being provided for allowing introduction of water for moisturizing the material or for extinguishing burning material, and with the other plug connector pipe being provided for applying a vacuum. As is further shown in FIG. 6, the coupler piece 24 is further provided with a relief valve 27, such as pressure relief valve or suction relief valve, which is suitably connectable to the appropriate plug connector pipe 25 or 26 if e.g. a vacuum should be provided in the container 1.

Extending parallel to the plug connector pipes 23, 25, 26 at the underside of the bottom 10 are ribs 28 which are slidably guided in complementary grooves 29 (indicated in dashdot lines) of the microwave apparatus 30. When charging the microwave apparatus 30, the container 1 is slid along the groove 29 until reaching a position in which the plug connector pipes 23, 24, 25 are in proper alignment with the coupler piece 24 and can be connected with the coupler piece 24 in tight manner.

Figure 7:
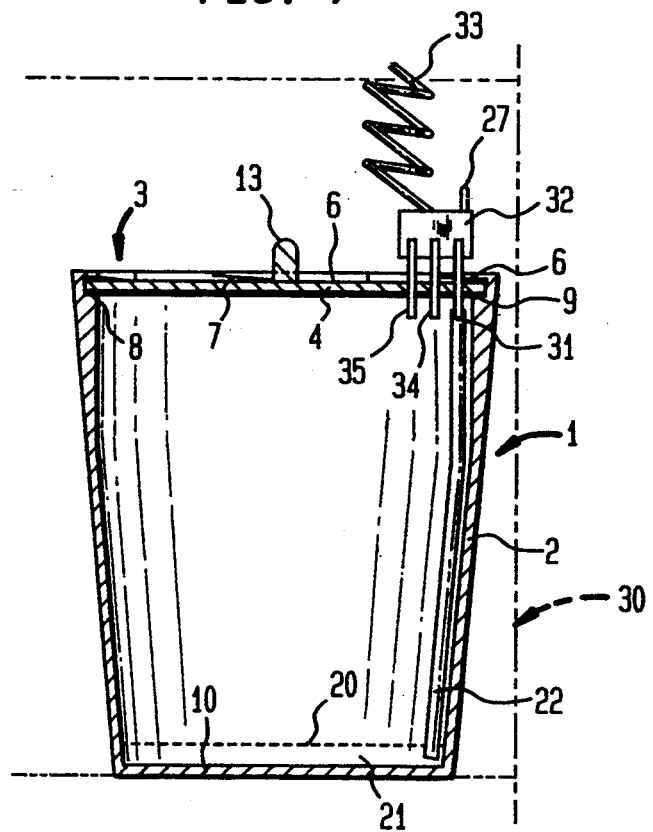
FIG. 7 is a schematic vertical section of still a further embodiment of a container according to the present invention.

FIG. 7 shows another embodiment of the container 1, with the riser 22 being mounted to a plug connector pipe 31 which is part of a unit which is incorporated in the lid 4 and further includes plug connector pipes 34, 35 for allowing attachment of e.g. a vacuum pump and an injector for introducing water or other liquid into the container 1. The unit of plug connectors 32, 34, 35 cooperates with a complementary coupler piece 32 which is part of the microwave apparatus 30 (indicated by dashdot lines) and supported by a flexible line 33 to allow positional adjustment during connection of the coupler piece 32 to the plug connectors 31, 34, 35. Like in the illustration of FIG. 1, the coupler piece 32 is also provided with a relief valve 27. By incorporating the unit of plug connector pipes 31, 34, 35 in the lid 4, additional provision of valves or other fittings at the lid of the container as shown in FIG. 6 can be omitted. The container 1 which is closed by the lid 4 can simply be placed in the microwave apparatus and the flexibly supported coupler piece 32 needs only be attached to the plug connector pipes.

Persons skilled in the art will understand that the plug connector pipes may also be used for introduction of gases. Further, the plug connector pipe for applying a vacuum inside the container, may also be used for supplying vapor, which exits the container, to a sensor for measuring the vapor fraction and/or smoke fraction in the outgoing air.

The container 1 according to FIG. 7 may be employed in a microwave oven which is provided with a turntable, with the turntable imparting an oscillating motion to the container. In order to prevent the container from falling off or sliding off the turntable, suitable ribs or engagement parts, as set forth in connection with the embodiment of FIG. 1, should be provided.

Although not shown in the drawing, the container 1 according to FIG. 7 may be further modified by mounting the riser 22 to the body 2 of the container 1 instead of to the plug connector 31. In order to attain a sufficient sealing effect between the riser pipe 22 and the plug connector 31 and to prevent leakage to the interior of the container 1, a sealing surface is provided between the lid 4 and the upper end of the riser 22 to attain an air-tight connection therebetween, whereby the plug connector pipe 31 is now flush with the inside wall surface of the lid 4. When closing the container 1 by turning the lid 4 in the bayonet mount 3, the plug connector pipe 31 is turned as well until being in alignment with the upper end of the riser 22 and bearing above the sealing surface of the upper end of the riser 22. Thus, liquid can be withdrawn in a same manner from the bottom of the container 1 through the riser 22. By fixedly securing the riser 22 to the body 2 of the container 1, a subsequent insertion of the riser 22—after positioning the container within the microwave apparatus—becomes unnecessary. That is advantageous, especially when the refuse inside the container is of relative compact composition.

Figure 8:
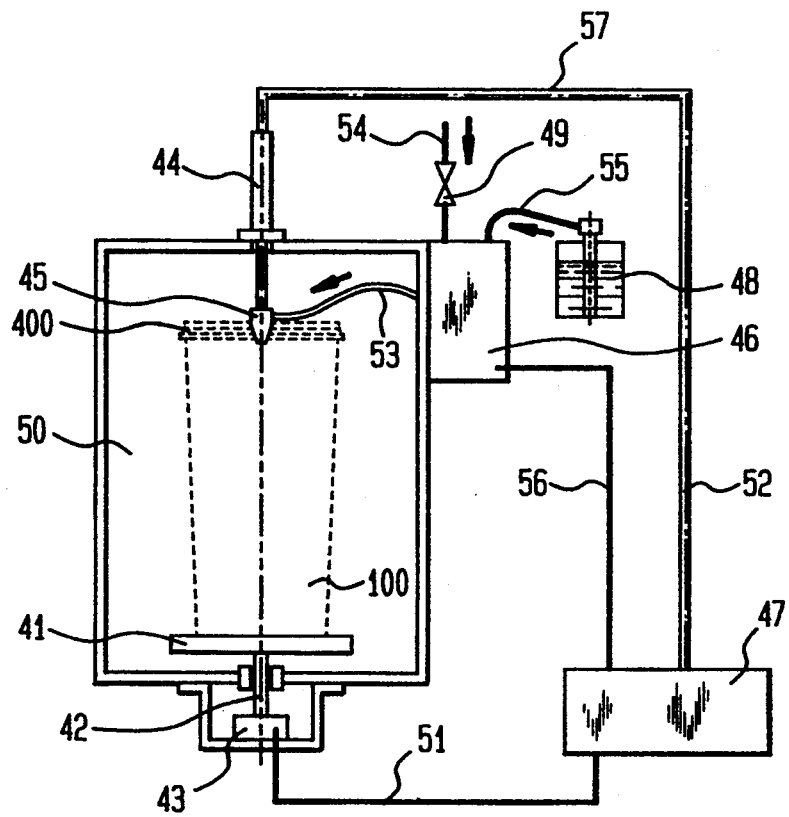
FIG. 8 is a simplified, schematic illustration of a microwave apparatus in accordance with the invention for treating material in a container.

Turning now to FIG. 8, there is shown a simplified, schematic illustration of a microwave apparatus in accordance with the invention for treating material in a container and for allowing a modification of conditions inside the container e.g. for spraying water or gas into the container.

An exemplary container 100, which is indicated by dashdot lines, is placed upon a scale plate 41 inside a treatment chamber 50 of the microwave apparatus. Although not shown in detail, the microwave apparatus may be of the type having a casing with three magnetrons by which the container 100 with the material is exposed to microwave energy. The arrangement of the magnetrons for use of the microwave apparatus as sterilizer or disinfector is such as to ensure that the entire treatment chamber 50 and thus the container 100 is evenly exposed to microwave radiation and to prevent the formation of cold spots and interferences.

The scale plate 41 is mounted on a weighing axle 42 which is supported upon a weighing cell 43. Although not shown in detail in the drawing, the scale plate 41 may be rotatably supported upon the weighing cell 43, with a pivot drive applying a reciprocating rotational motion to the scale plate 41 in order to attain a better mixing and even heating of material, e.g. waste water or kitchen waste, during treatment with or without additives.

A line 51 operatively connects the weighing cell 43 with a microprocessor-operated control unit 47 which is connected to an actuator 44 via a line 52. The actuator 44 regulates a water injector unit 45, with its nozzle head being arranged in an opening of the lid 400 of the container 100. The water injector 45 is connected to a mixer 46 via a feed conduit 53. Water is supplied to the mixer 46 via a conduit 54 in which a solenoid valve 49 is interposed for controlling the water supply. A conduit 55 is further connected to the mixer 46 for supply of an additive such as disinfectant and/or odorant from a tank 48. Line 56 operatively connects the mixer 46 with the control unit 47.

Figure 11:
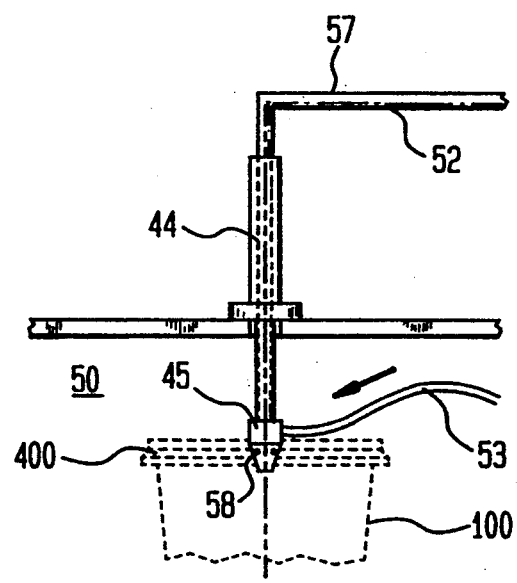
FIG. 11 is a fragmentary illustration of the microwave apparatus of FIG. 8, showing in detail an injector unit for adding a liquid into a container.

As further shown in FIG. 8, and in particular in FIG. 11, which shows a detailed fragmentary view of the injector 45, the nozzle head is provided with sensors 58 by which physical parameters such as temperature, pressure, moisture etc. and/or chemical parameters such as composition, pH value etc. can be determined. An example of such a sensor 58 is a temperature probe which is directly situated in the area of the wall surface of the nozzle head projecting into the interior of the container 100. Suitably, in this area, the material of the wall surface of the nozzle head is impervious to microwaves and of sufficient heat conducting material. Also, the nozzle head of the water injector 45 may incorporate a pressure sensor, with areas of the wall surface of the nozzle head or even the entire area of the nozzle head projecting into the container 100, acting as pressure sensor membrane. The information determined by the sensors 58 is supplied to the microprocessor-operated control system 47 via a control line 57.

The water injector 45 may include other sensors as well which are also protected from high frequency fields, such as oxygen electrodes, pH electrodes or the like.

Figure 9:
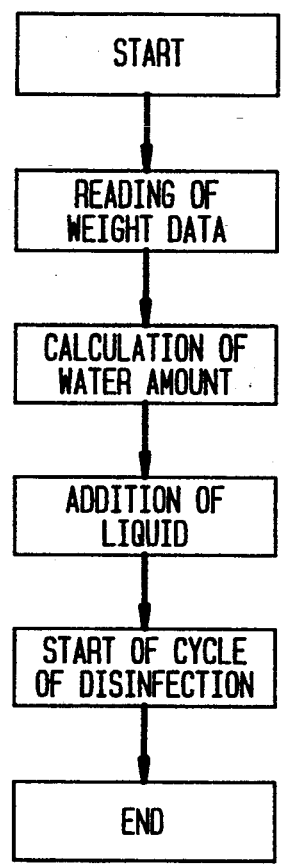
FIG. 9 is a schematic block diagram illustrating the steps for treating material in a microwave apparatus in accordance with the invention.
Figure 10:
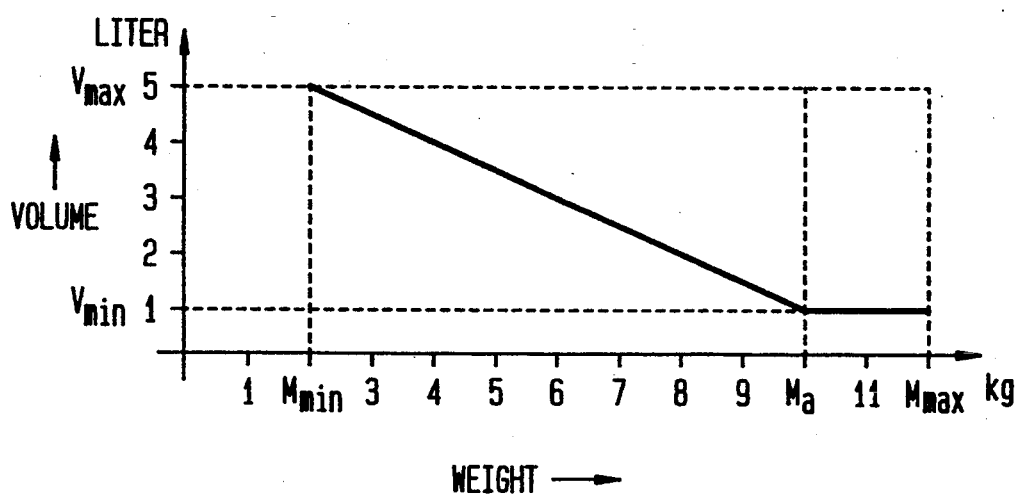
FIG. 10 is a graphical illustration of the amount of water to be added as a function of the weight of refuse to be disinfected.
Figure 12:
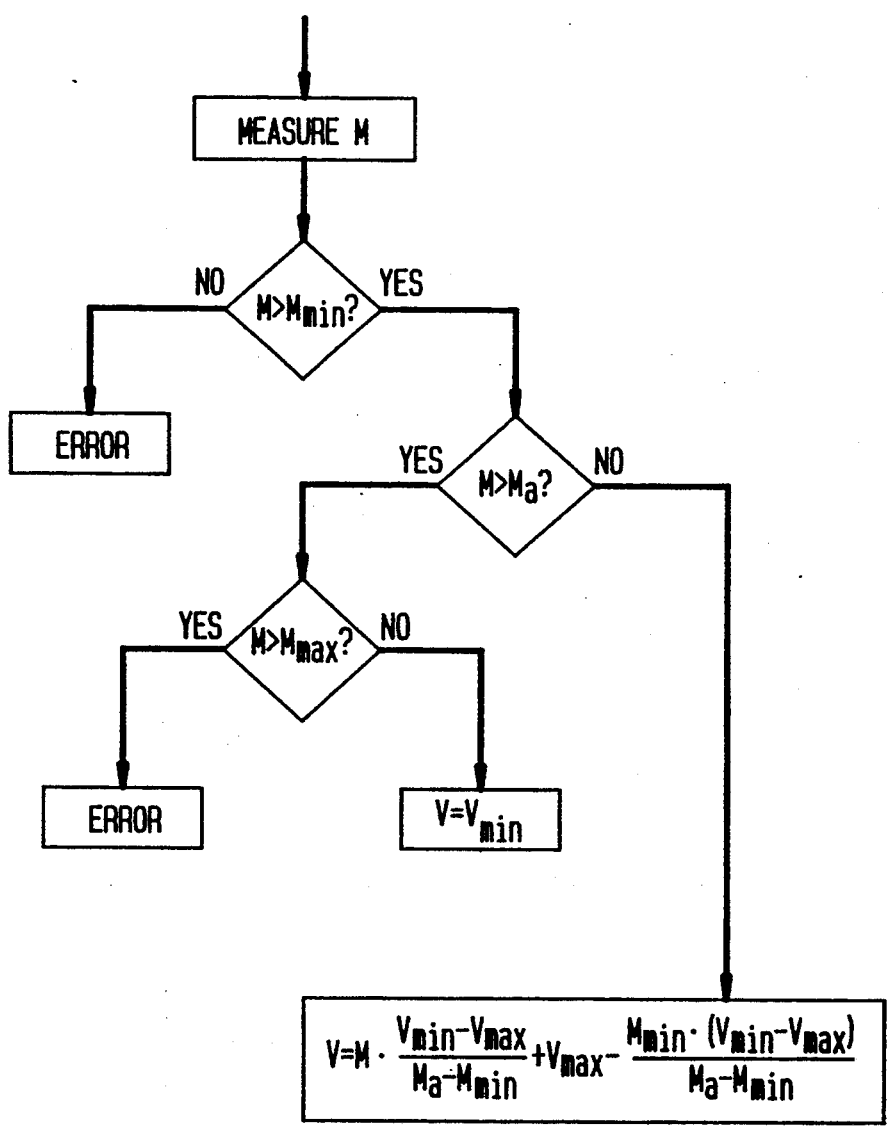
FIG. 12 is a schematic flow diagram of the calculating steps and illustration of the formula for determining the quantity of water as a function of the measured weight.

At operation of the microwave apparatus according to the invention for heating, disinfecting or sterilizing of material, the container 100 with the material is placed on the scale plate 41 and the system is switched on. As indicated in particular by the flow diagram of FIG. 9, after starting the unit, the weight of the material-filled container 100 is determined by the weighing cell 43. Since the container 100 has a given standard weight, the actual weight of the material within the container 100 can be determined via the weighing cell 43 or other electronic scale. Possible "false values" can be used for detecting error situations. When the weighing cell 43 recognizes a correct weight reading, the amount of water is calculated in accordance with the graphical illustration of FIG. 10 which shows the amount of water to be added as a function of the weight of refuse to be disinfected. Persons skilled in the art will understand that the graph is calculated in accordance with an algorithm, with consideration of empirical values as can be seen from FIG. 12 which shows a schematic flow diagram of the calculating steps and illustrates the formula for determining the quantity of water as a function of the measured weight M.

In general, not more than 10 kg refuse are contained in a container so that this value $M_a$ is assumed as limit, which means that to each container of more than 10 kg weight (up to $M_{max}$), not more than 1 liter ($V_{min}$) or one unit of water is added. Experience shows that a realistic minimum amount $M_{min}$ of refuse is about 2 kg, with the weight of the container being approx. 1.5 kg and the weight of the refuse being approx. 0.5 kg. In this case, i.e. at a weight of 2 kg, 5 liter ($V_{max}$) (5 units) of liquid should be added. In the event, the container 100 (or bucket) as placed on the scale plate 41 has an overall weight of 4 kg, the amount of water to be added is 4 liter as indicated by the graph in FIG. 10.

After calculating the amount of water to be added, the required amount of water, possibly with addition of additives from tank 48, is injected via the nozzle head of the injector 45 into the container 100. Subsequently, the usual cycle for heating, disinfecting, or sterilizing is started in a suitable manner until the system is turned off.

Persons skilled in the art will understand that the water can be added into the container also outside the treatment chamber 50 after the weight of the container has been determined so that the injector 45 and the actuator 44 can be omitted. Such a manual addition of water is, however, less desirable because it does not permit addition of water during operation if such becomes necessary.

A further modification of the microwave apparatus according to the invention is attained by inputting data into the weighing cell 43 and the control program of the microprocessor 47 in accordance with the material to be treated. In this manner the process is synchronized to the type of refuse to be treated i.e. whether e.g. light refuse such as cellulose to be sterilized or the like, or heavy refuse such as kitchen garbage or metal objects is to be treated.

Suitable disinfectants and/or odorants for disinfecting refuse through microwave radiation include citric acids or lemon oil because these compounds generate their effectiveness especially at increased temperatures while cold citric acid or cold lemon oil are completely harmless at normal use. A further reason for using citric acid as disinfectant and/or odorant is the ease by which the refuse can be disposed after sterilization or disinfection because citric acid is not harmful to the waste water. The addition of disinfectant and/or odorants may be carried out in dependence on the amount of injected water as controlled by the microprocessor so as to ensure that the material to be treated includes a sufficient concentration of disinfectant and/or odorant. This is achieved by adding an amount of disinfectant and/or odorants to the mixing chamber of mixer 46 in dependence of the water content in the container 100. In the event a container 100 with a large amount of liquid is placed upon the scale plate 1, the liquid supplied from the mixer 46 to the injector 45 includes a higher concentration of disinfectant and/or odorant because of the subsequent dilution in the container. On the other hand, if the material to be treated is dry, water is introduced through conduit 54 into the mixing chamber of the mixer 46 and fed to the nozzle of injector 45 and into the container via conduit 53 in which disinfectant and/or odorants are already present and thus diluted by the water fed through conduit 53. Thus, in absolute terms, the concentration remains constant for each situation.

Figure 13:
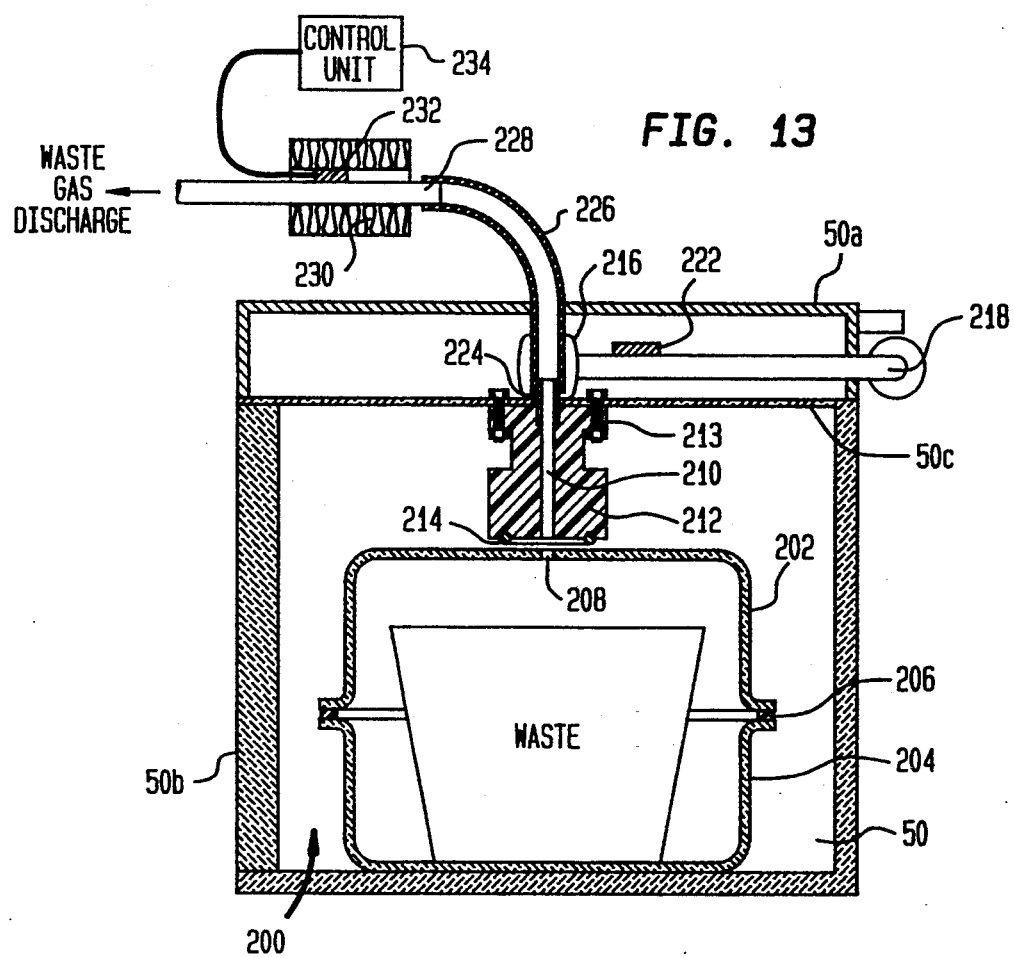
FIG. 13 is a schematic illustration of another embodiment of a microwave apparatus according to the invention, with a modified container for placement in a treatment chamber of the microwave apparatus.

Turning now to FIG. 13, there is shown another embodiment of a container for use in a microwave apparatus, generally designated by reference numeral 200 and containing material such as waste for treatment, such as sterilization or disinfection, by means of microwave radiation.

For sake of simplicity, the microwave apparatus is illustrated only by way of the treatment chamber 50 which is part of a frame 50a and includes an access door 50b. Persons skilled in the art will understand that the microwave apparatus must contain much mechanical apparatus which does not appear in the foregoing Figures. For example, the apparatus must be equipped with magnetrons to produce microwave radiation. However, these elements, like much other necessary apparatus, are not part of the present invention, and thus have been omitted from the Figures.

The container 200 is made of rigid microwave-pervious material such as glass, porcelain, plastic or the like and includes a lower shell 204 and an upper shell 202 which are sealingly closeable with each other via an interposed elastic annular seal 206. The upper shell 202 is provided in its top face with a central bore 208 which is in communication with a passageway 210 of a clamp block or hold down element 212.

As shown in FIG. 13, the clamp block 212 is attached to the top wall 50c of the treatment chamber 50 by means of screwed connections 213 and sandwiched between the top wall 50c and the opposite top face of the upper shell 202. The top wall 50c is characterized by a certain elasticity to allow flexure thereof. At its side facing the upper shell 202, the clamp block 212 is provided with a rubber ring 214 to allow tight fit of the clamp block 212 onto the upper shell 202.

Figure 14:
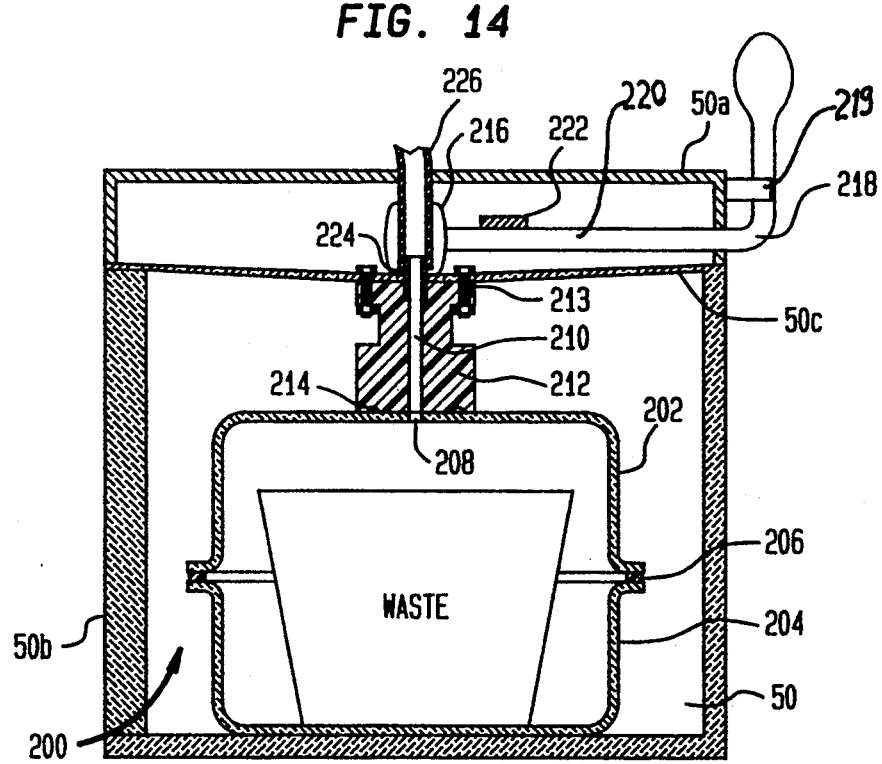
FIG. 14 is a side view onto the microwave apparatus of FIG. 13, with a side wall of the treatment chamber being removed.

As shown in FIG. 14 which is a side view of the microwave apparatus, with a side wall of the treatment chamber 50 being removed to allow illustration of the interior thereof, the clamp block 212 is acted upon by an eccentric cam 216 which is actuated by a clamping lever 218. A shaft 220 operatively connects the lever 218 to the eccentric cam 216 and is supported in the frame 50a of the microwave apparatus and by a bracket 222 which extends across the top wall 50c of the treatment chamber 50, as shown in FIG. 15 which is a front view of the microwave apparatus, with the front door 50b of the treatment chamber 50 being opened.

Figure 15:
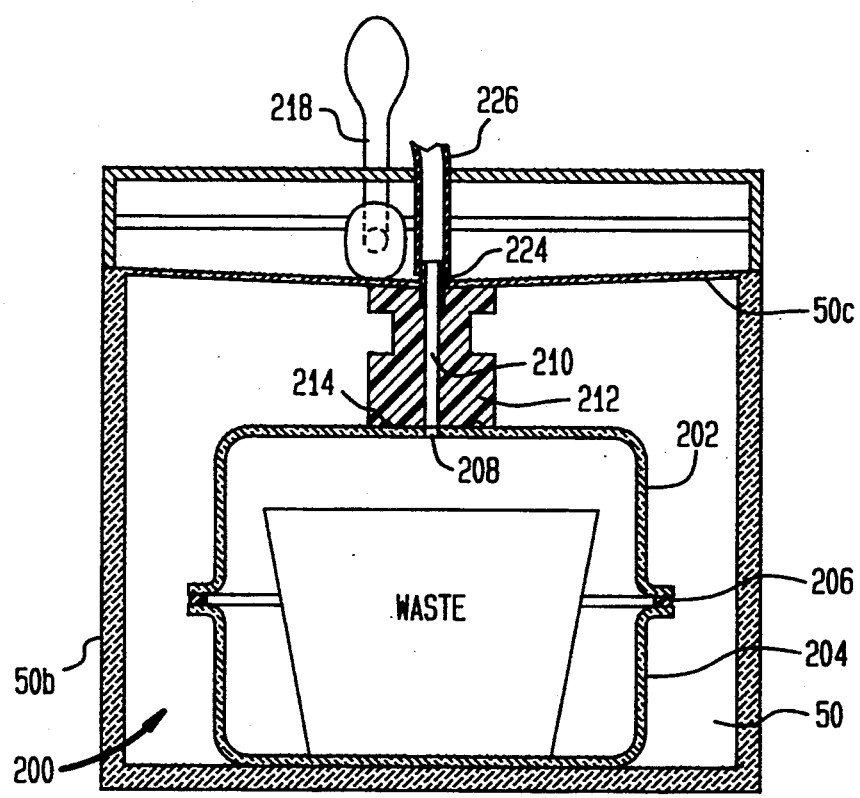
FIG. 15 is a frontal view onto the microwave apparatus, with the access door of the treatment chamber being opened.

When actuating the clamping lever 218, the eccentric cam 216 rolls upon the elastic top wall 50c of the treatment chamber 50 and causes a sagging thereof to thereby force the clamp block 212 with its rubber ring 214 downwardly against the upper shell 202 (see FIGS. 14 and 15). Thus, the upper shell 202 is firmly pressed against the lower shell 204 and the container 200 is tightly closed, with the bore 208 being in communication with the passageway 210.

In this closing position, the eccentric cam 216 is moved beyond its dead center, with the clamping lever 218 bearing upon a stop member 219 to avoid a further movement of the eccentric cam 216 and thus unintentional opening of the container 200 during operation of the microwave apparatus.

Persons skilled in the art will understand that the use of an eccentric cam to firmly press the clamp block 212 onto the upper shell 202 is described by way of example only and may certainly be substituted by other means such as e.g. a toggle lever, without departing from the scope of the invention.

As further seen in FIG. 13, a sleeve 224 is partly fitted in the container-distal end of the clamp block 212 and traverses the top wall 50c of treatment chamber 50 to extend the passageway 210 outwardly. A short hose 226 of flexible material is placed with one end thereof over the sleeve 224. The other end of the hose 226 is connected to a pipe 228 which is enclosed over a major portion thereof by an insulation 230 and leads to the outlet for waste gas (steam or condensate) generated inside the container 200 during microwave radiation.

A temperature sensor 232 is placed directly onto the outside of the pipe 228 for measuring the temperature of the wall surface of the pipe 228, and thus for indirectly determining the temperature of the waste gas passing through the pipe 228. The temperature sensor 232 generates a signal commensurate with the detected temperature and transmits this signal to a control unit 234 for regulating operation of the microwave apparatus e.g. for controlling the energy supply (magnetrons) of the microwave apparatus.

At operation, the waste placed inside the container 200 is heated through microwave radiation. Waste gas generated during heating of the waste exits through the bore 208 and aligned passageway 210 and flows via the hose 226 through the pipe 228. The temperature sensor 232 determines the temperature of the wall surface of the pipe 228 to generate a corresponding signal which is fed to the control unit 234. If the actual value of the temperature as measured by the sensor 232 exceeds a predetermined desired value, the control unit 234 e.g. cuts the energy supply to the magnetrons.

While the invention has been illustrated and described as embodied in a microwave apparatus, and container for use in a microwave apparatus, it is not intended to be limited to the details shown since various modifications and structural changes may be made without departing in any way from the spirit of the present invention.

What is claimed as new and desired to be protected by Letters Patent is set forth in the appended claims:

1. Apparatus for heating, disinfecting or sterilizing materials by means of microwave radiation, comprising:
   a treatment chamber;
   a container disposed in said treatment chamber, said container having a lower container part and an upper container part sealingly closable with each other to form an interior for housing materials to be subjected to microwave radiation in said treatment chamber, said upper container part having a bore;
   clamping means for sealingly securing said upper container part to said lower container part, said clamping means including a passageway means, said passageway means being aligned with said bore for directly connecting the interior of said container to an area outside said treatment chamber for allowing waste gas forming inside said container during exposure to microwave radiation to exit therethrough;
   measuring means operatively connected to said passageway means for providing a signal commensurate with the temperature of waste gas exiting therethrough; and
   control means operatively connected to said measuring means for evaluating the signal of said measuring means and controlling a level of the microwave radiation.

2. An apparatus as defined in claim 1 wherein said treatment chamber has an elastic top wall, said clamping means including a clamp block sandwiched between said upper container part and said top wall, an eccentric cam running on said top wall opposite to said upper container part, and a clamping lever actuating said eccentric cam for forcing said clamp block downwards to thereby firmly press said upper container part onto said lower container part.

3. An apparatus as defined in claim 1 wherein said measuring means includes a heat-insulated pipe connected to said upper container part for passage of exiting waste gas, and a temperature sensor placed onto said heat-insulated pipe.

* * * * *